United States Patent
Stearns et al.

(10) Patent No.: US 9,950,127 B2
(45) Date of Patent: Apr. 24, 2018

(54) FILTER INTERFACE FOR MULTIMODAL SURGICAL GAS DELIVERY SYSTEM

(71) Applicant: SurgiQuest, Inc., Milford, CT (US)

(72) Inventors: Ralph Stearns, Bozrah, CT (US); Dennis Feldman, Apollo Beach, FL (US); Raymond Y. Tang, Rosemead, CA (US)

(73) Assignee: Surgiquest, Inc., Milford, CT (US)

( * ) Notice: Subject to any disclaimer, the term of this patent is extended or adjusted under 35 U.S.C. 154(b) by 0 days.

(21) Appl. No.: 14/674,835

(22) Filed: Mar. 31, 2015

(65) Prior Publication Data

US 2015/0202391 A1    Jul. 23, 2015

Related U.S. Application Data

(60) Division of application No. 13/862,851, filed on Apr. 15, 2013, now Pat. No. 9,067,030, which is a
(Continued)

(51) Int. Cl.
*A61M 13/00* (2006.01)
*A61B 17/34* (2006.01)
(Continued)

(52) U.S. Cl.
CPC ....... *A61M 13/003* (2013.01); *A61B 17/3421* (2013.01); *A61B 17/3474* (2013.01);
(Continued)

(58) Field of Classification Search
CPC ............ A61B 17/3421; A61B 17/3474; A61B 2017/00221; A61B 2017/00225;
(Continued)

(56) References Cited

U.S. PATENT DOCUMENTS 4,735,603 A   4/1988 Goodson et al.
7,182,752 B2  2/2007 Stubbs et al.
(Continued)

FOREIGN PATENT DOCUMENTS

DE    4219859 A1   12/1993
EP    2482869 A1   8/2012
(Continued)

OTHER PUBLICATIONS

Supplemental Search Report dated Sep. 8, 2014 in connection with EP Application No. 11827365.
(Continued)

*Primary Examiner* — Imani Hayman
(74) *Attorney, Agent, or Firm* — Locke Lord LLP; Scott D. Wofsy

(57) ABSTRACT

A surgical gas delivery system is disclosed that includes a device housing supporting a control unit and a filter interface having a seat for receiving a filter cartridge, the filter cartridge having a filter housing defining an interior reservoir, wherein sensors are coupled to the control unit for sensing a level of liquid within the reservoir of the filter cartridge to prevent contamination of the device, and wherein a set of blocking valves are provided in the device housing for interacting with the filter cartridge when it is received in the filter interface to control flow through suction and pressure lines of the device, and wherein the control unit is adapted to recognize a characteristic of the filter cartridge received in the filter interface.

4 Claims, 8 Drawing Sheets

Related U.S. Application Data continuation of application No. 13/237,628, filed on Sep. 20, 2011, now Pat. No. 9,375,539.

(60) Provisional application No. 61/384,412, filed on Sep. 20, 2010.

(51) Int. Cl.
*B01D 46/00* (2006.01)
*B01D 46/42* (2006.01)
*A61M 1/00* (2006.01)
*A61B 90/98* (2016.01)
*A61B 17/00* (2006.01)
*A61B 90/00* (2016.01)

(52) U.S. Cl.
CPC .......... *A61B 90/98* (2016.02); *A61M 1/0031* (2013.01); *A61M 13/00* (2013.01); *A61M 13/006* (2014.02); *B01D 46/0008* (2013.01); *B01D 46/4254* (2013.01); *A61B 2017/00221* (2013.01); *A61B 2017/00225* (2013.01); *A61B 2090/064* (2016.02); *A61B 2218/008* (2013.01); *A61M 2205/33* (2013.01); *A61M 2205/70* (2013.01); *A61M 2205/75* (2013.01)

(58) Field of Classification Search
CPC ........ A61B 2019/448; A61B 2019/464; A61B 2218/008; A61M 13/00; A61M 13/006; B01D 46/0008; B01D 46/4254
See application file for complete search history.

(56) References Cited

U.S. PATENT DOCUMENTS

| | | |
|---|---|---|
| 7,250,035 B1 | 7/2007 | Ott et al. |
| 7,285,112 B2 | 10/2007 | Stubbs et al. |
| 7,338,473 B2 | 3/2008 | Campbell et al. |
| 7,413,559 B2 | 8/2008 | Stubbs et al. |
| 7,854,724 B2 | 12/2010 | Stearns et al. |
| 2005/0140759 A1 | 6/2005 | Hilton et al. |
| 2006/0129087 A1* | 6/2006 | Uesugi et al. ................. 604/26 |
| 2007/0000300 A1* | 1/2007 | Diemunsch ......... A61M 13/003 73/1.02 |
| 2007/0088275 A1 | 4/2007 | Stearns et al. |
| 2007/0249990 A1 | 10/2007 | Cosmescu |
| 2010/0185139 A1 | 7/2010 | Stearns et al. |
| 2011/0028891 A1* | 2/2011 | Okoniewski ....... A61B 17/3423 604/26 |

FOREIGN PATENT DOCUMENTS

| | | |
|---|---|---|
| JP | 2005-287840 | 10/2005 |
| WO | WO-20100042204 A2 | 4/2010 |
| WO | WO-201141387 A1 | 4/2011 |

OTHER PUBLICATIONS

Translation of Office Action for Japanese Patent Application No. JP2013-529418, dated Jun. 23, 2015.

\* cited by examiner

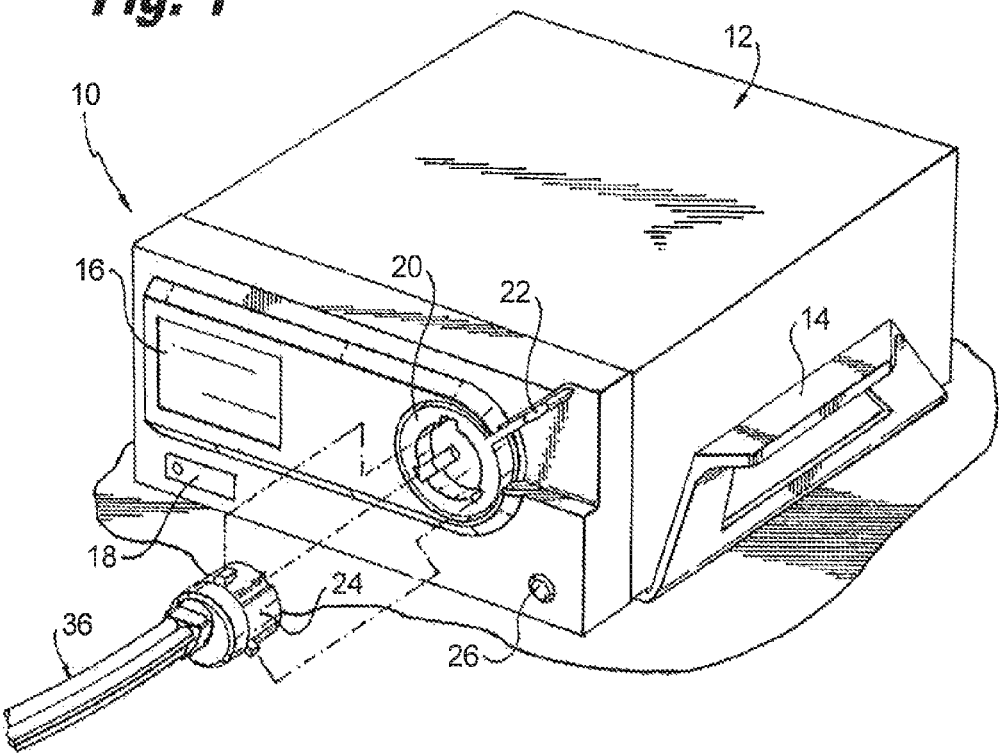
Fig. 1
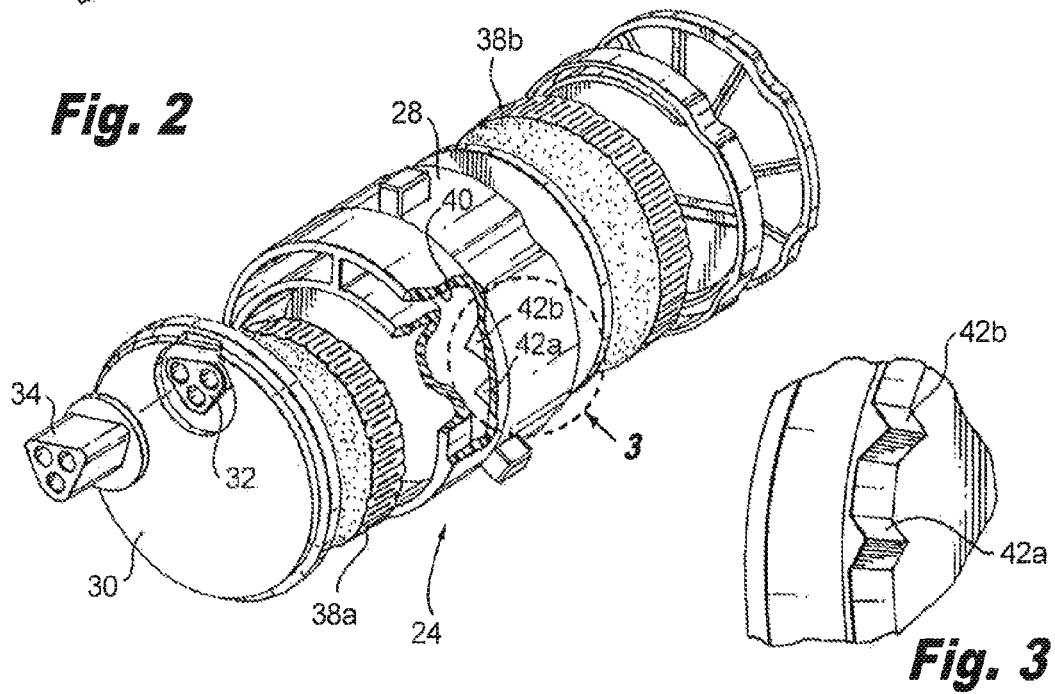
Fig. 2
Fig. 3

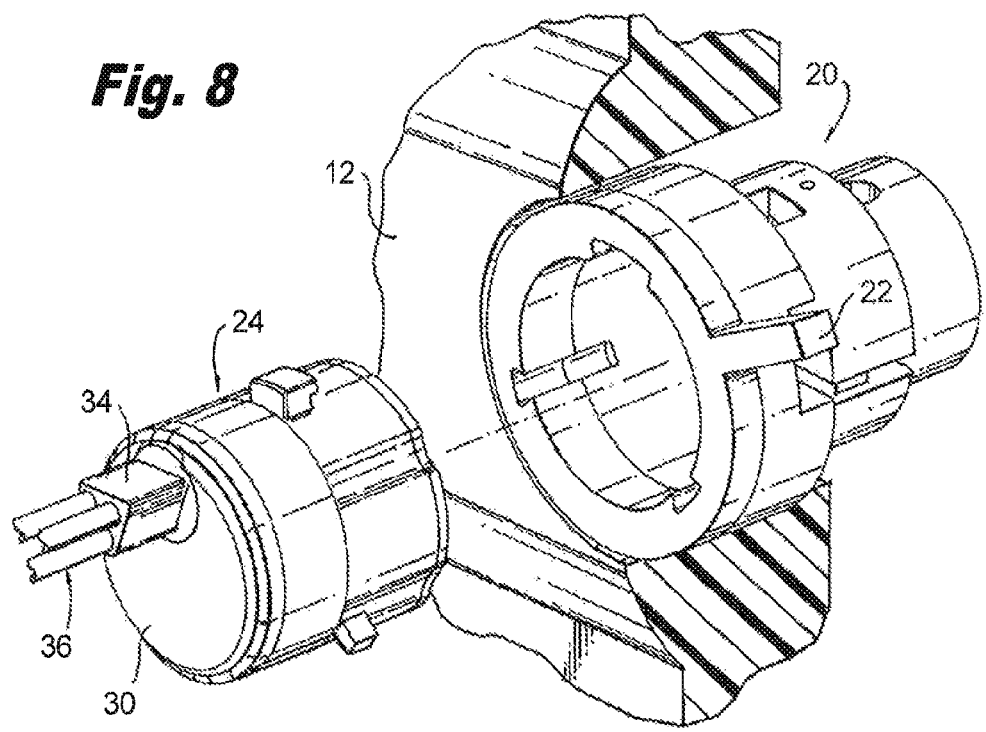
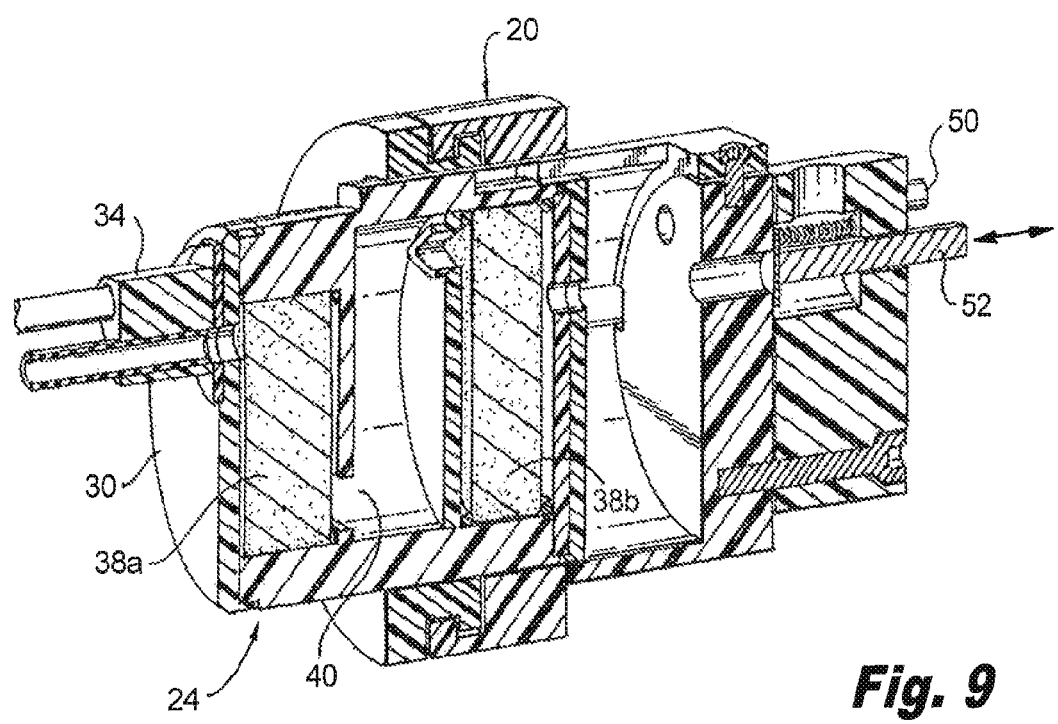

FILTER INTERFACE FOR MULTIMODAL SURGICAL GAS DELIVERY SYSTEM

CROSS-REFERENCE TO RELATED APPLICATION

The subject application is a divisional of U.S. patent application Ser. No. 13/862,851 filed on Sep. 7, 2012, which is a continuation of U.S. patent application Ser. No. 13/237,628, which claims priority to U.S. Provisional Application No. 61/384,412 filed on Sep. 20, 2011.

BACKGROUND OF THE INVENTION

1. Field of the Invention

The subject invention is directed to laparoscopic surgery, and more particularly, to a filter interface for a multimodal insufflation system used during laparoscopic surgical procedures.

2. Description of Related Art

Laparoscopic or "minimally invasive" surgical techniques are becoming commonplace in the performance of procedures such as cholecystectomies, appendectomies, hernia repair and nephrectomies. Benefits of such procedures include reduced trauma to the patient, reduced opportunity for infection, and decreased recovery time. Such procedures within the abdominal (peritoneal) cavity are typically performed through a device known as a trocar or cannula, which facilitates the introduction of laparoscopic instruments into the abdominal cavity of a patient.

Additionally, such procedures commonly involve filling or "insufflating" the abdominal (peritoneal) cavity with a pressurized fluid, such as carbon dioxide, to create what is referred to as a pneumoperitoneum. The insufflation can be carried out by a surgical access device (sometimes referred to as a "cannula" or "trocar") equipped to deliver insufflation fluid, or by a separate insufflation device, such as an insufflation (veress) needle. Introduction of surgical instruments into the pneumoperitoneum without a substantial loss of insufflation gas is desirable, in order to maintain the pneumoperitoneum.

During typical laparoscopic procedures, a surgeon makes three to four small incisions, usually no larger than about twelve millimeters each, which are typically made with the surgical access devices themselves, typically using a separate inserter or obturator placed therein. Following insertion, the inserter is removed, and the trocar allows access for instruments to be inserted into the abdominal cavity. Typical trocars often provide means to insufflate the abdominal cavity, so that the surgeon has an open interior space in which to work.

The trocar must provide a means to maintain the pressure within the cavity by sealing between the trocar and the surgical instrument being used, while still allowing at least a minimum freedom of movement of the surgical instruments. Such instruments can include, for example, scissors, grasping instruments, and occluding instruments, cauterizing units, cameras, light sources and other surgical instruments. Sealing elements or mechanisms are typically provided on trocars to prevent the escape of insufflation gas. Sealing elements or mechanisms typically include a duckbill-type valve made of a relatively pliable material, to seal around an outer surface of surgical instruments passing through the trocar.

Further, in laparoscopic surgery, electrocautery and other techniques (e.g. harmonic scalpels) create smoke and other debris in the surgical cavity, reducing visibility by fogging the view from, and coating surfaces of endoscopes and the like. A variety of surgical insufflation systems and smoke evacuation systems are known in the art.

Additionally, SurgiQuest, Inc., Milford, Conn. USA has developed surgical access devices that permit access to an insufflated surgical cavity without conventional mechanical seals, and has developed related systems for providing sufficient pressure and flow rates to such access devices, as described in whole or in part in U.S. Pat. No. 7,854,724.

The present invention relates to multimodal systems, and related devices and methods, capable of performing multiple surgical gas delivery functions, including insufflation to standard or specialized surgical access devices or other instruments, such as veress needles and the like, smoke evacuation through standard or specialized surgical access devices, and specialized functions, such as recirculation and filtration of insufflation fluids, such as with the above-mentioned surgical access devices described in U.S. Pat. No. 7,854,724, as well as those in U.S. Pat. Nos. 7,182,752, 7,285,112, 7,413,559 or 7,338,473, for example.

Use of a single multimodal system such as those described herein reduces costs by requiring purchase of only one system while achieving multiple functions, and also thereby reduces the amount of equipment needed in an operating room, thus reducing clutter and allowing space for other necessary equipment.

SUMMARY OF THE INVENTION

The subject invention is directed to a new and useful surgical gas delivery system for use during laparoscopic surgical procedures, and more particularly, to a unique filter interface for a multimodal insufflation and smoke evacuation system. The system includes a device housing supporting a computer-controlled control unit and a filter interface. The filter interface has a seat for receiving a disposable filter cartridge. The filter cartridge has a filter housing defining an interior reservoir, and means are coupled to the control unit for sensing a level of liquid within the reservoir of the filter cartridge.

The means for sensing a level of liquid within the reservoir includes a first sensor adapted and configured to detect a first liquid level within the reservoir and a second sensor adapted and configured to detect a second liquid level within the reservoir. Preferably, each sensor is a reflective sensor with an integrated infrared emitter and photodiode.

The filter cartridge has a pair of optical prisms formed integral with the housing and located within the reservoir for sensing a level of liquid within the reservoir. Preferably, the pair of prisms includes a first prism defining a first set point level and a second prism defining a second set point level. An outer surface of the filter housing located proximate the location of the prisms is in optical communication with the means for sensing a level of liquid within the reservoir when the filter is seated within the filter interface.

The control unit is adapted and configured to provide a warning indicating that a liquid level within the reservoir has reached the first set point level. The control unit is adapted and configured to shut down a compressor within the device housing when a liquid level within the reservoir has reached the second set point level.

The device housing also includes a normally closed spring-loaded blocking valve for blocking a suction line associated with the smoke evacuation feature when a filter cartridge is not seated within the filter interface, or in other operational modes. In addition, the device housing includes a normally closed spring-loaded blocking valve for blocking a pressure line associated with the gaseous sealing features when a filter cartridge is not seated within the filter interface, or in other operational modes.

The device is adapted and configured to perform a self-test prior to a surgical procedure, to determine if there is a filter cartridge attached to the filter interface. The blocking valves are both closed during the self-test. The device has a first mode of operation in which the blocking valves for the suction line and pressure line are both closed. This corresponds to a standard or conventional insufflation mode of operation in which a standard or conventional trocar is employed.

As used herein, the terms conventional or standard trocar shall refer to a mechanically sealed trocar device that employs, for example, a duckbill seal, tri-cuspid seal or wiper seal to prevent the egress of insufflation fluid from the body cavity through the trocar during a surgical procedure, as opposed to a gas sealed trocar that does not employ a mechanical seal to prevent the egress of insufflation fluid through the trocar.

The device has a second mode of operation in which the blocking valves for the suction line and pressure line are both open. This corresponds to a gaseous sealing mode of operation, wherein smoke evacuation is performed while a unique gas sealed trocar device in employed. The device has a third mode of operation in which the suction line and pressure line are both open, but the pressure line is internally blocked by the filter. This corresponds to an insufflation and smoke evacuation mode of operation wherein two conventional trocars are employed in tandem.

The control unit of the surgical gas delivery device of the subject invention is also adapted to detect or otherwise recognize an operational or physical characteristic of the filter cartridge received in the filter interface. More particularly, the control unit is adapted to detect whether the filter cartridge is configured for use in a mode of operation in which a gas sealed trocar device is connected to the filter cartridge through a multi-lumen tube set (i.e., the gaseous seal mode), or whether the filter cartridge is configured for use in a second mode of operation in which two conventional or standard mechanically sealed trocar devices are connected to the filter cartridge through a multi-lumen tube set (i.e., the insufflation and smoke evacuation mode). The control unit is also adapted to detect the orientation or position of the filter cartridge within filter interface, to ensure the filter cartridge is properly seated prior to operation.

In another aspect of the subject invention, the device housing of the surgical gas delivery device communicates with the abdominal cavity of a patient through a gas circuit, which includes a surgical access device. The device housing of the surgical gas delivery device supports a computer-controlled control unit having a gas sensor for monitoring gas quality in the gas circuit. The gas sensor is adapted and configured to detect gas composition in the gas circuit. For example, the gas sensor can be adapted to detect the $CO_2$, $O_2$ or $N_2$ concentration within the gas circuit. The gas composition in the gas circuit correlates directly with the gas composition within the abdominal cavity. More particularly, the gas composition within a recirculation chamber of the surgical access device correlates directly with the gas composition within the abdominal cavity of the patient.

Preferably, the control unit is adapted and configured to maintain a gas concentration in the abdominal cavity within a predetermined range, as monitored by the gas sensor. The control unit is adapted and configured to increase insufflation flow rate to the abdominal cavity if the gas sensor determines the gas concentration in the abdominal cavity falls below a predetermined level.

These and other features of the surgical gas delivery system of the subject invention and the manner in which it is manufactured and employed will become more readily apparent to those having ordinary skill in the art from the following enabling description of the preferred embodiments of the subject invention taken in conjunction with the several drawings described below.

BRIEF DESCRIPTION OF THE DRAWINGS

So that those skilled in the art to which the subject invention appertains will readily understand how to make and use the subject invention without undue experimentation, preferred embodiments thereof will be described in detail herein below with reference to certain figures, wherein:

FIG. 1 is a perspective view of a multimodal gas delivery device constructed in accordance with a preferred embodiment of the subject invention;

FIG. 2 is an exploded perspective view of a filter cartridge adapted and configured for interfacing with the gas delivery device of FIG. 1, which includes a fluid trap or reservoir for capturing bodily fluid drawn into the filter cartridge during use;

FIG. 3 is an enlarged localized view of a pair of optical prisms formed integral with the filter housing and located within the reservoir for sensing a level of liquid within the reservoir;

FIG. 8 is an enlarged localized view of the multimodal gas delivery device of FIG. 1, with the front face cut away to reveal the internal components of the filter interface, including the latching lever, filter seat and blocking valves;

FIG. 9 is a cross-sectional view of the filter cartridge seated in the cartridge interface and interacting with the blocking valves;

DETAILED DESCRIPTION OF PREFERRED EMBODIMENTS

Figure 4:
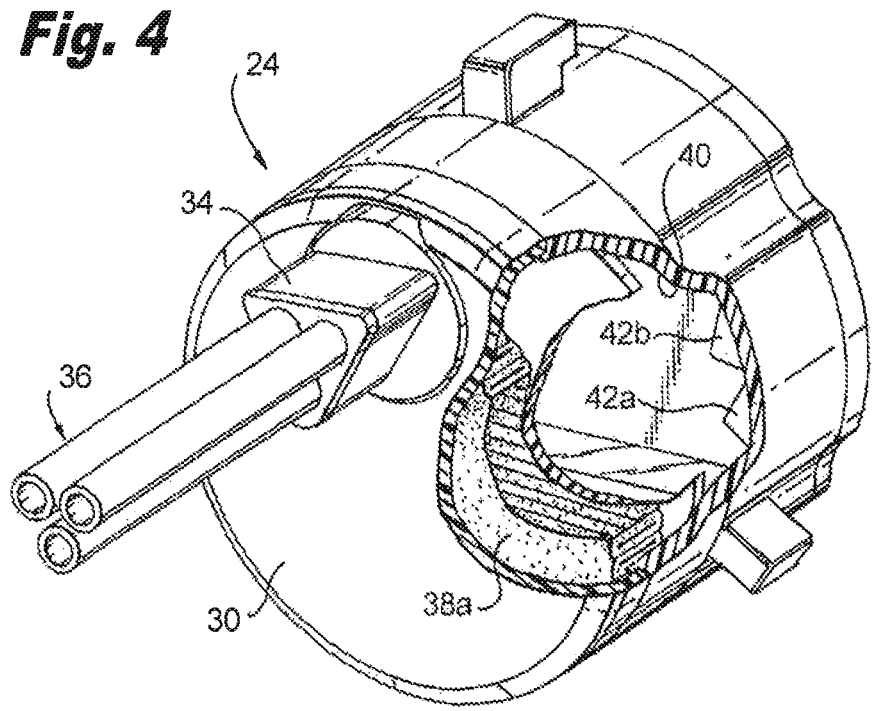
FIG. 4 is a perspective view of the filter cartridge with the outer wall of the filter housing broken away to show the reservoir having a level of fluid therein that is insufficient to interact with the first optical prism.

It is to be appreciated that the systems, devices and methods presented herein may be used for surgical gas delivery, including insufflation, smoke evacuation, and/or recirculation in connection with suitable surgical devices, and in applicable surgical procedures. The present invention is particularly suited for minimizing the amount of equipment needed in a surgical operating room, in that the subject systems are capable of performing multiple functions, and therefore also allow flexibility of surgical technique. It is envisioned that the gas delivery system disclosed herein can be used in general laparoscopic procedures including but not limited to laparoscopic cholecystectomy, laparoscopic appendectomy, laparoscopic hernia repair, Nissen-Y and Lap Nephrectomy.

Those skilled in the art will readily appreciate that systems described in U.S. Pat. No. 7,854,724, for example, provide pressurized gas to and remove depressurized gas from specialized surgical access devices, which penetrate into a surgical cavity, such as a patient's abdominal cavity. These access devices are adapted and configured to form a pressure barrier to inhibit the loss of insufflation gas to the atmosphere.

Gas from the abdomen interchanges with gas coming from the access device(s), a portion of which is collected and recycled through the system, and is re-pressurized, passing through one or more filters along the way. During this recycling process, smoke and/or other circulating debris, such as atomized fluids, are removed by the filters, improving visibility within the surgical cavity, thus aiding in the surgical procedure.

The multimodal gas delivery system of the subject invention is adapted and configured to selectively provide three different insufflation functions. The first mode of operation involves the automatically (electronically) regulated delivery of a pressurized insufflation fluid to a gas sealed access device to provide and maintain sealable access to the body cavity, and smoke evacuation from the body cavity through a filter device. In this mode, the user can selectively start and stop insufflation, set the abdominal pressure, select the level of smoke evacuation (normal ~3 l/min or high ~8 l/min), and set the flow rate. A unique three lumen tube set is used for this mode of operation, wherein one lumen is used for pressure, one lumen is used for suction and one lumen is used for insufflation.

In this mode, the gas sealed access device includes an annular nozzle configured to direct pressurized fluid from a plenum chamber into a central bore of a trocar to provide a constant gaseous seal around a surgical instrument inserted there through, while simultaneously preventing a loss of pressurized fluid from the body cavity through the central bore of the trocar. Such a surgical access device is disclosed in U.S. Pat. Nos. 7,413,559 and 7,854,724, which are both herein incorporated by reference in their entireties.

The second mode of operation utilizes two tethered conventional trocars and involves directing pressurized insufflation gas into the body cavity using one conventional trocar to create and maintain the pneumoperitoneum, while performing smoke evacuation through the second conventional trocar that is in fluid communication with a filter device. In this mode, the device evacuates gas from the peritoneum through a lumen connected to the suction line of a compressor. The evacuated gas is filtered and returned to the insufflation line. A two lumen tube set is used for this mode of operation, wherein one lumen is used for standard insufflation and one lumen is used for smoke evacuation. In this mode, the user can select the level of smoke evacuation (normal ~3 l/min or high ~8 l/min) and selectively start and stop smoke evacuation.

The third mode of operation can be considered a conventional insufflation mode, which is conducted with a single conventional trocar, using a standard insufflation tube set that is adapted to interface with a standard 6 mm insufflation connector on the front face of the device housing. The compressor and all other gas circuits related to the gas sealed access device are shut off during this mode of operation. In this mode, the user can selectively start and stop insufflation. Three different flow rates can be selected by the user within a range of 1 to 40 l/min, and the values of each level can be changed by the user.

Referring now to the drawings, wherein like reference numerals identify similar structural features or aspects of the subject invention, there is illustrated in FIG. 1 a preferred embodiment of a surgical gas delivery system for use during laparoscopic surgical procedures which is designated generally by reference numeral 10. The system 10 includes a device housing 12 with carrying handles 14 on each side of the housing. The front face of the housing 12 has a capacitive or resistive touch screen 16 for presenting a graphical user interface GUI and a power switch 18 for turning the device on and off.

The front face of housing 12 further includes a filter cartridge interface 20 with a rotatable latch mechanism 22 configured to facilitate the secure engagement of a disposable filter cartridge 24 within the device housing 12. In addition, the front face of housing 12 includes a standard 6 mm insufflation connection 26. While not shown, the rear face of the housing 12 includes a gas supply fitting for connection with a source of compressed gas, a standard USB interface for service purposes and a standard power connection.

The filter cartridge interface 20 is designed to recognize which type of filter 24 has been inserted into the housing. For example, it may recognize the proper position or orientation of the filter cartridge. It can also recognize if the inserted filter is specifically designed for use in the first mode of operation (i.e., the gaseous seal mode) or a filter specifically designed for use in the second mode of operation (i.e., insufflation and smoke evacuation mode).

Referring to FIG. 2, the filter cartridge 24 has a filter housing 28 that includes a cover plate 30 having a manifold connection 32 for receiving a fitting 34 associated with a tri-lumen tube set 36 (see FIG. 1). The filter housing 28 is dimensioned and configured to support a pair of filter elements 38a and 38b, and it defines an interior reservoir or fluid trap 40 for collecting bodily fluid that has been drawn into the system through the suction line of the tube set 36 during smoke evacuation, for example.

As best seen in FIG. 3, a pair of triangular optical prisms 42a, 42b formed integral with the filter housing 28 and located within the reservoir 40 for sensing a level of liquid within the reservoir 40. Preferably, the first or lower prism 42a defines a first set point level for the sensing system and the second or upper prism 42b defines a second set point level for the sensing system. More particularly, the first prism 42a is positioned to detect a first liquid level within reservoir 40 and the second prism 42b is positioned to detect a second liquid level within reservoir 40.

Figure 5:
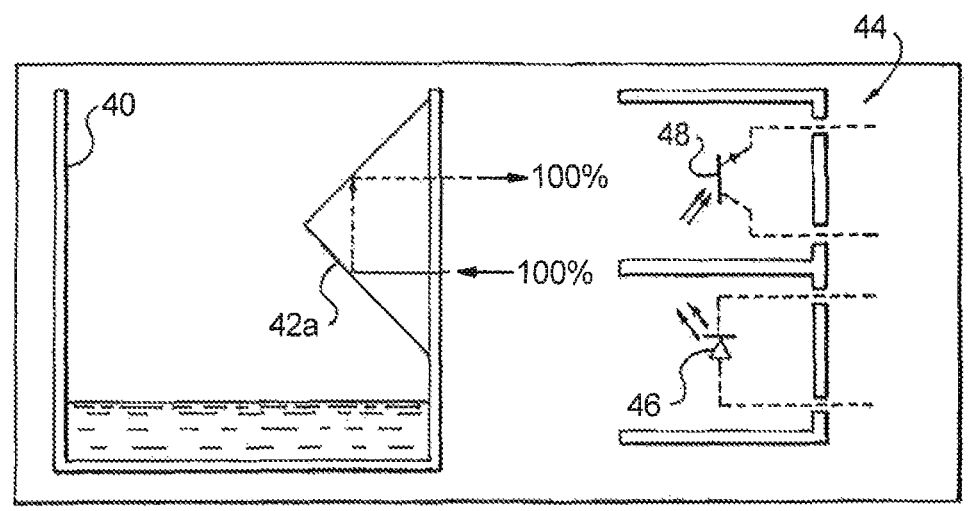
FIG. 5 is a schematic illustration of the first optical prism and the electronic sensor associated therewith, when fluid is not interacting with the prism, as shown in FIG. 4, whereby 100% of the emitted infrared signal is returned through the prism to the photodiode of the sensor.

Referring to FIG. 5, each optical prism 42a, 42b is operatively associated with a fluid level sensor 44 that comprises an analog-output reflective sensor with an integrated high efficiency infrared emitter 46 and a photodiode 48 housed in a small form factor SMD package (e.g., HSDL-9100, manufactured by Avago Technologies, Ft. Collins, Colo.). In operation, an infrared signal is generated by the emitter 46 and directed into an optical prism 42a, 42b. If, as illustrated in FIG. 4, the prism 42a is not covered by liquid in reservoir 40, it will return 100% of the emitted infrared signal to the photodiode 48, as depicted schematically in FIG. 5.

Figure 6:
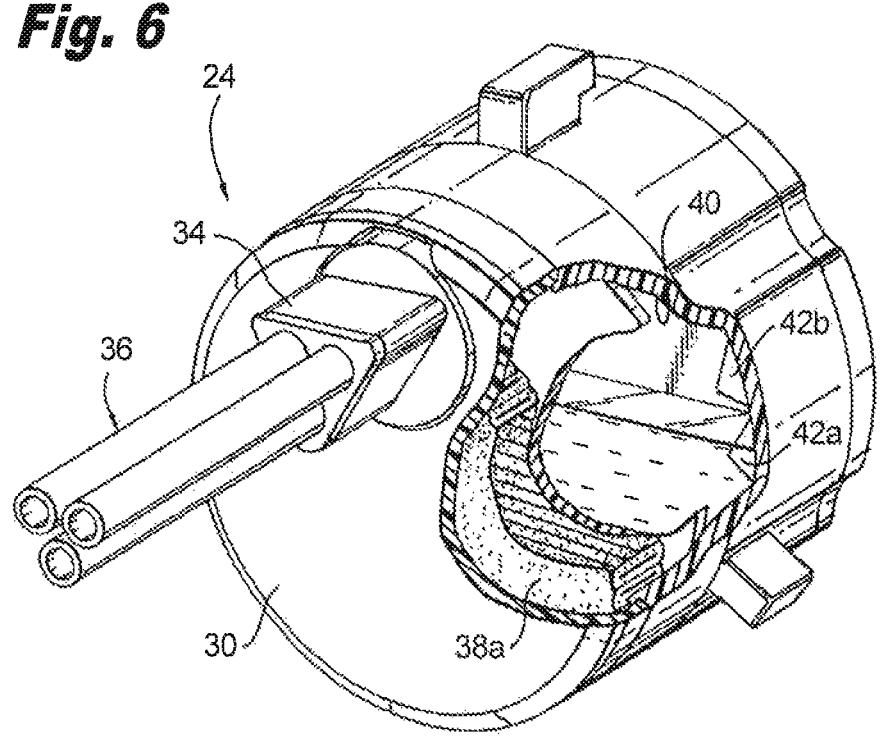
FIG. 6 is a perspective view of the filter cartridge with the outer wall of the filter housing broken away to show the reservoir having a level of fluid therein that is sufficient to interact with the first, optical prism.
Figure 7:
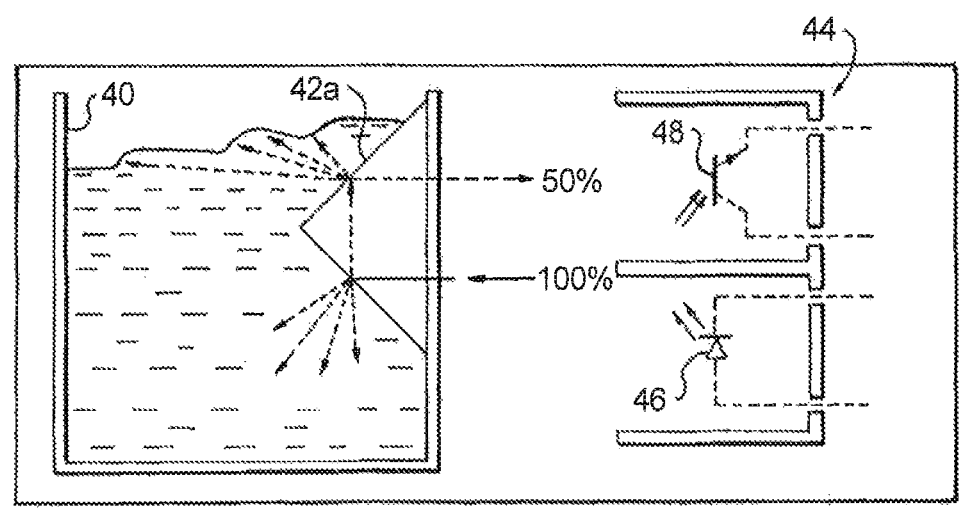
FIG. 7 is a schematic illustration of the first optical prism and the electronic sensor associated therewith, when fluid is interacting with the prism, as shown in FIG. 6, whereby less than 100% of the emitted infrared signal is returned through the prism to the photodiode of the sensor.

If however, as illustrated in FIG. 6, the prism 42a is covered by liquid in reservoir 40, a portion of the infrared light delivered by the emitter 46 will be scattered into the fluid, and the prism will return less than 100% of the emitted infrared signal to the photodiode 48 (e.g., 50% of the signal), as depicted schematically in FIG. 7. In this case, the controller will provide a visual and/or audible warning to the user indicating that the liquid level within the reservoir 40 has reached the first set point level. This will ensure early user attention/action and prevent contamination of the device housing 12. As discussed in more detail below with respect to FIG. 10, the controller or control unit is adapted and configured to shut down a compressor associated with the suction line within the device housing 12 when a liquid level within the reservoir 40 of the filter housing 24 has reached the second set point level.

In sum, the liquid level sensors 42a, 42b will detect two states, when the filter reservoir 40 is filled to about a first level and when the filter reservoir 40 is filled to about a second level. When the filter reservoir 40 is filled to about the first level, information is sent to the controller to show a warning. When the reservoir 40 is full, to prevent the device housing 12 from contamination, the compressor will shut down immediately within 0.2 second. The controller also informed and it will show a warning. The device 10 then switches to a standard insufflation mode of operation, without smoke evacuation.

Referring now to FIGS. 8 and 9, the filter interface 20 of the device housing 12 further includes a pair of spring-loaded blocking valves 50, 52, which are adapted and configured to interact with the filter cartridge 24 when it is seated in the filter interface 20. More particularly, these mechanical blocking valves 50, 52 are closed, if no filter is connected. The valves are opened when the filter cartridge 24 is seated in the filter interface 20. Blocking valve 50 is associated with the suction line used for smoke evacuation, while blocking valve 52 is associated with the pressure line used for effectuating a gaseous seal in a unique gas sealed trocar.

Figure 10:
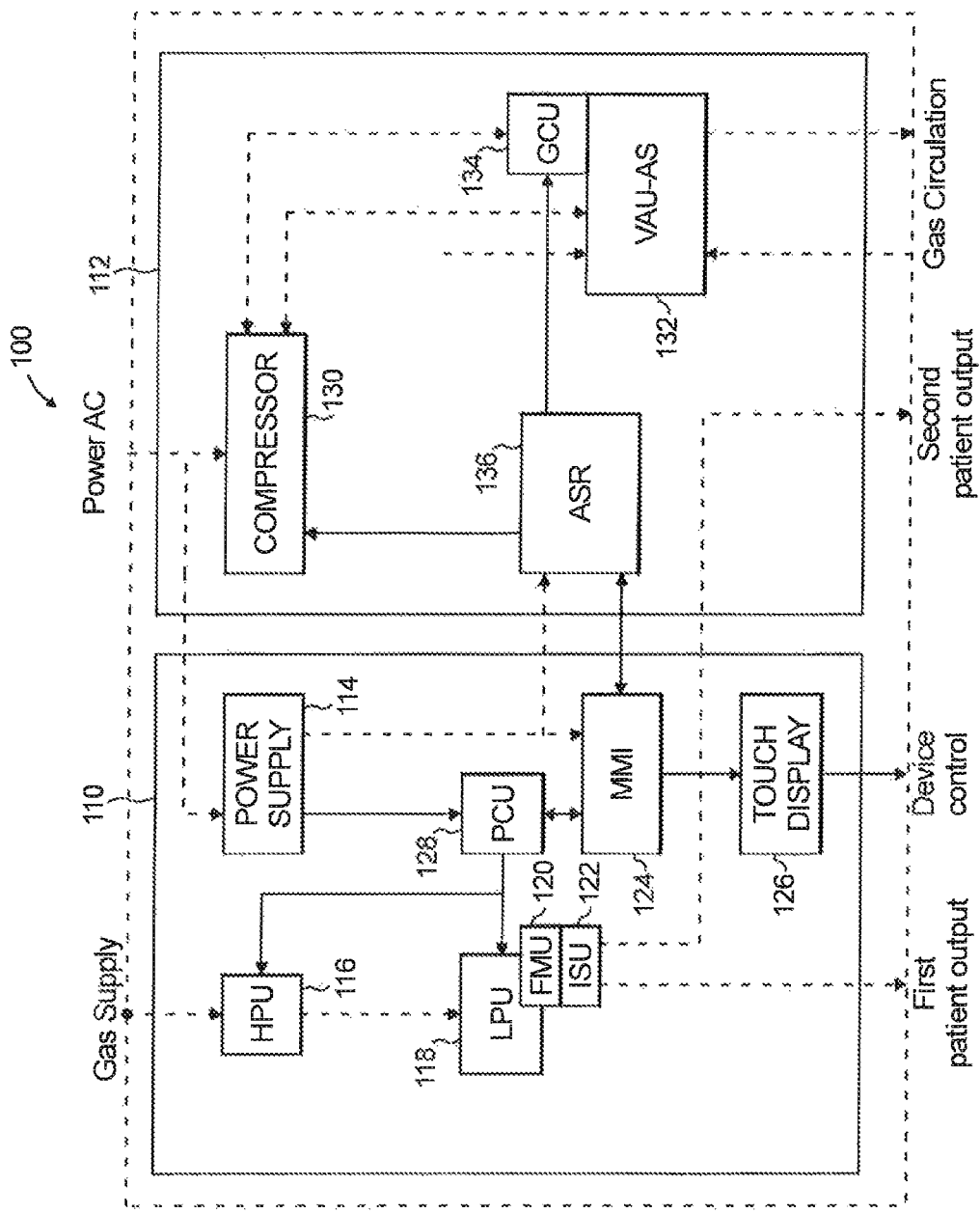
FIG. 10 is a block diagram, of the components of the multimodal gas delivery device illustrated in FIG. 1.

Referring to FIG. 10, the gas delivery system 100 of the subject invention includes two primary component blocks 110 and 112. The first component block 110 includes a power supply 114, a High Pressure Unit (HPU) 116 designed to reduce incoming pressure from the gas supply to ~2.2 bar, and a Low Pressure Unit (LPU) 118 that controls insufflation output. It also contains access points for measuring abdominal pressure and it includes a mechanical relief valve. The LPU includes a Flow Measurement Unit (FMU) 120 for differential pressure measurement and an Insufflation Split Unit (ISU) 122 that divides the insufflation path into two outlines, namely Outlet Line Valves (OLV1 and OLV2), (see FIG. 11).

A man machine interface (MMI) or single board computer 124, which is based on a Windows CE operating system, is responsible for controlling the graphical user interface presented on the Touch Display 126, which is preferably a 7" graphic display screen, as shown in FIG. 1. A Primary Control Unit (PCU) 128 defined on a printed circuit hoard controls the HPU, LPU, FMU and ISU of component block 110. In addition, the PCU observes both fluid level sensors associated with the filter interface 20.

The second component block 112 includes a compressor 130 responsible for pressure within the gas circuit of the system. It can supply the gas sealed trocar with flow up to 55 l/min at 35 psi. The output of the pressure line is controlled by a bypass valve (BPV). Component block 112 further includes a Valve Actuation Unit (VAU-AS) 132 that contains the different valves which control the flow of gas through the system. More particularly, the VAU-AS controls the performance the relief valve for an overpressure scenario (ORV) and the high pressure gas fill valve (GFV) needed for the self-test mode, among others. The self-test feature will be discussed in more detail herein below. The VAU-AS also provides an alternative outlet for the smoke evacuation function (SEV), and access points for pressure measurement. It also cools down the gas in the pressure line.

With continuing reference to FIG. 10, the second component block 112 further includes a Gas Composition Unit (GCU) 134 that consists of an oxygen sensor and an Air Seal Regulator (ASR) 136, which is a printed circuit board, that essentially controls the valves of the VAU-AS and enables/disables the compressor 130. It also measures pressure in the gas circuit and analyzes the output of the GCU. More particularly, the GCU 134 defects oxygen concentration in the gas circuit to ensure gas quality, as discussed in more detail below.

More particularly, the ASR 136 measures pressure in the pressure line and controls the relief valve associate therewith. It measures the temperature of the device housing 12 and controls two cooling fans. It controls the relief valve in an over pressure scenario and the gas fill valve GFV. It also controls the air ventilation valve AVV (see FIG. 11), which is needed for the smoke evacuation mode and it communicates with the PCU/MMI. The VAU-AS also control the status of the filling level indicator in the filter 24, recognizes the type of installed filter and the correct locked position of the filter 24 in the filter interface 20 of device housing 12.

During a laparoscopic surgical procedure, the gas concentration in the abdominal cavity should be maintained at a predetermined level. This level can change during a procedure for two reasons: a) leakages from the abdominal cavity can cause air to be drawn into the abdominal cavity through the trocar; and b) leakages in the suction line of the compressor can cause air to be returned to the trocar.

Figure 13:
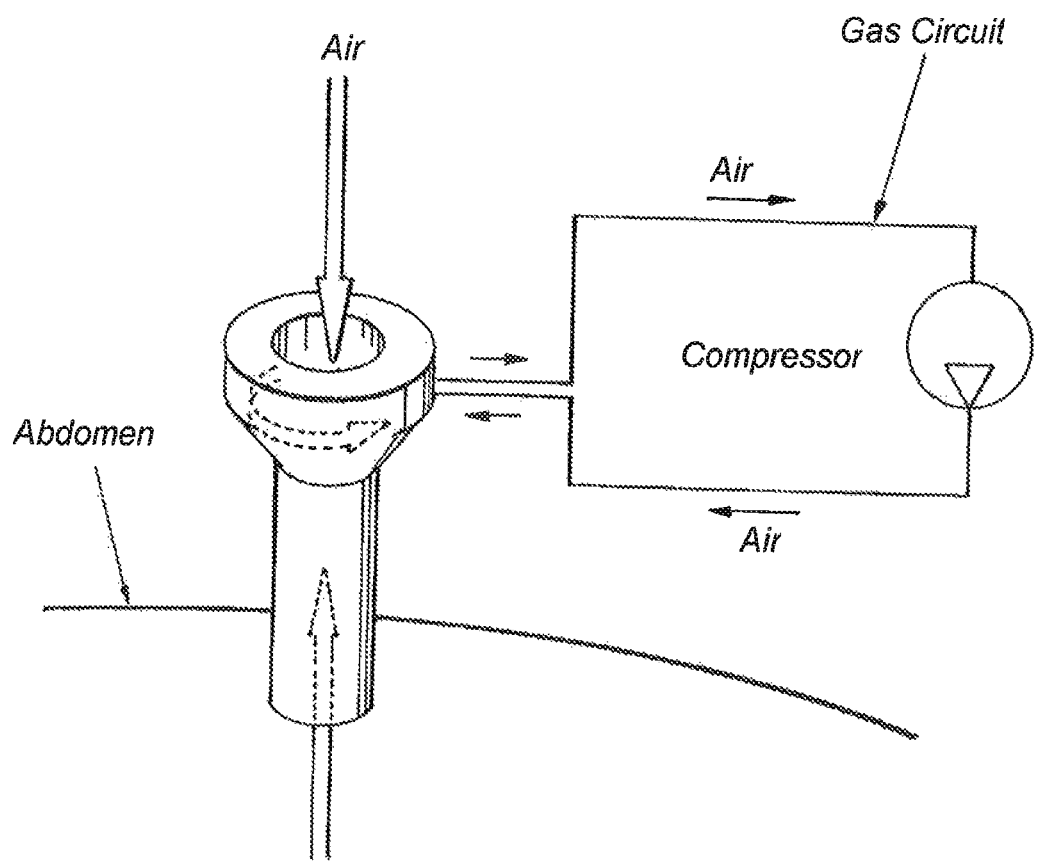
FIG. 13 depicts the gas circuit of the subject invention, which is monitored by a gas composition sensor, for ensuring gas quality in the abdominal cavity of a patient during a laparoscopic surgical procedure.

It has been determined that the gas quality in the gas circuit of the gas delivery system 100, which is depicted in FIG. 13, correlates directly with the gas quality within the abdominal cavity of the patient. For example, it has been shown that a certain defined sensor value of oxygen in the gas circuit, as determined by GCU 134, results in a corresponding abdominal $CO_2$ concentration. The ASR 136 is adapted and configured to maintain gas concentration in the abdominal cavity within a predetermined range. The ASR 136 is adapted and configured to increase insufflation flow rate to the abdominal cavity if the gas concentration in the abdominal cavity falls below a predetermined level, as a result of leakage. The flow rate will not however, be lower than the selected smoke evacuation level. If the system is not able to recover gas quality on the abdominal cavity by increasing insufflation flow rate a message will be displayed and an audible alarm will be sounded.

Figure 11:
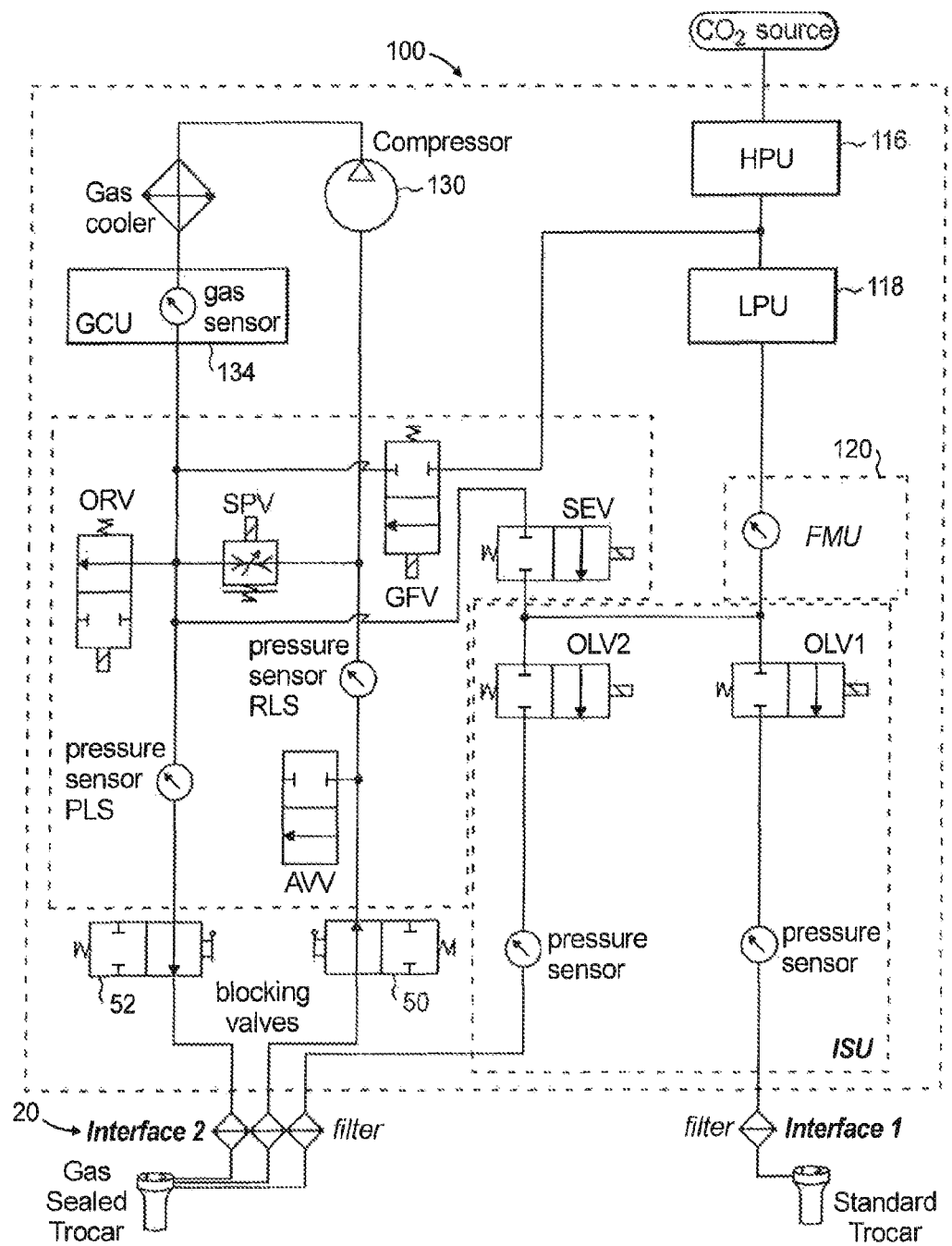
FIG. 11 is a detailed pneumatic schematic of the multimodal gas delivery system of the subject invention.

With continuing reference to FIG. 10 and in conjunction with FIG. 11, the gas delivery system 100 is adapted and configured to perform a self-test prior to a surgical procedure. For the self-test, two prerequisites are necessary. The gas supply must be connected to the device, and there can be no filter cartridge attached to the filter interface. If the filter is attached or the gas supply is empty the device will show an error message. In the self-test mode, the blocking valves 50, 52 for the pressure line and the suction line are closed. At this time, the BPV is open, the ORV is open and the GPV is open until pressure is not rising in the circuit. The device 100 will test for leakage in the system, compressor function, all valve functions, the pressure sensors the Low Pressure Safety Valve (LSV), the GCU and the FMU. If the self-test succeeds, the device starts up in normal mode. Otherwise a corresponding error message is shown on the user interface screen.

In the standard insufflation mode of operation, there is no filter in use. Thus, the blocking valves 50, 52 for the suction and pressure lines are both closed. Also closed are the GFV, BPV and SEV valves. The ORV is open and the OLV2 is closed. Depending upon the insufflation situation, the OLV1 may be open or closed.

Referring to FIG. 11, in the gaseous seal mode, the OLV1 is closed. The blocking valves 50, 52 for the suction line and pressure line are both open. The SEV, BPV and GRV valve are all closed. The BPV controls output and the OLV2 is open or closed depending upon the insufflation situation. The ASR will detect that a gas sealed trocar device is connected to the system. If the ASR detects a gas sealed trocar device, the time between measurement tasks is minimized to get faster information about abdominal pressure from the PCU. If the actual pressure is lower than the set pressure, the ASR will close the proportional bypass valve BPV. To reduce pressure in the abdomen the BPV is opened.

Figure 12:
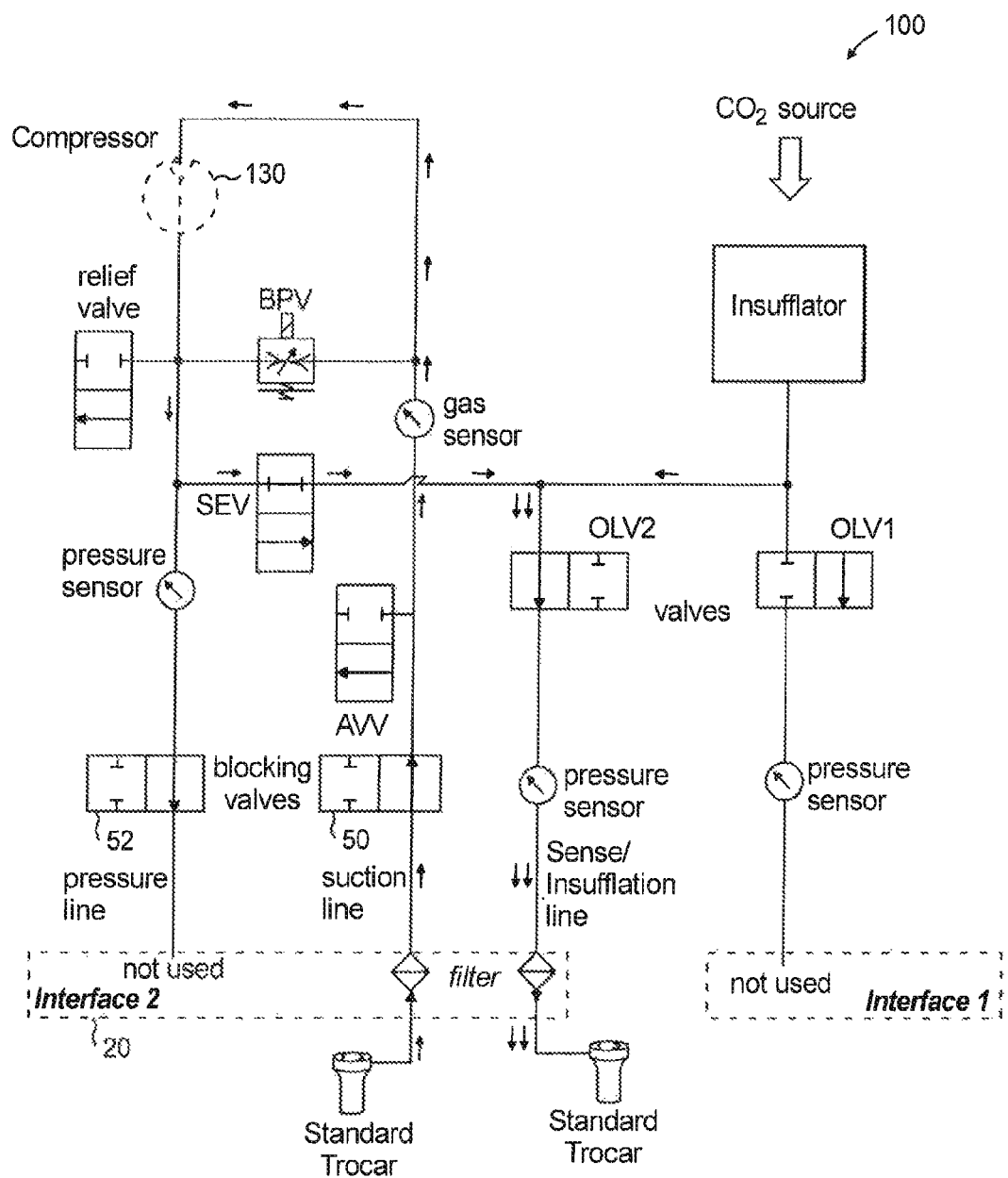
FIG. 12 is a pneumatic schematic of the multimodal gas delivery system of the subject invention during the insufflation mode with smoke evacuation, wherein two conventional mechanically sealed trocars are employed.

Referring to FIG. 12, in the insufflation and smoke evacuation mode, where two standard/conventional trocars are utilized with a unique two lumen tube set, the outlet line valve (OLV1) is closed. The compressor 130 is turned on and the blocking valve 50 of the suction line is open. In the insufflation and smoke evacuation mode, the filter 24 is seated in the filter interface 20. Accordingly, the blocking valves 50, 52 are both open. However, the blocking valve 52 associated with the pressure line remains blocked internally by the filter 24 itself. In this mode, the GPV, BPV and ORV are all open. The OLV2 is open or closed depending upon the insufflation situation. The power of smoke evacuation can be adjusted by the BPV. The SEV is open during insufflation and closed during a measurement task.

It is also envisioned and well within the scope of the subject disclosure that in the insufflation and smoke evacuation mode shown in FIG. 11, the ORV can be open rather than closed as shown. Consequently, no recirculation would occur. In such a configuration, one of the trocars would be used for smoke evacuation and removal, while the other trocar would only be used to provide $CO_2$ to the abdominal cavity and would not be connected to the pressure line of the pump.

While the subject invention, has been shown and described with reference to preferred embodiments, those skilled in the art will readily appreciate that various changes and/or modifications may be made thereto without departing from the spirit and scope of the subject invention as defined by the appended claims.

What is claimed is:

1. A surgical gas delivery device configured for insufflation and smoke evacuation through a gas sealed trocar having a recirculation chamber therein, the device comprising:
a device housing communicating with a patient's abdominal cavity through a gas circuit that includes a recirculation chamber of a gas sealed trocar and a compressor for circulating gas to and from the recirculation chamber of the trocar, the device housing supporting a computer-controlled control unit having an oxygen gas sensor for monitoring oxygen gas concentration in the gas circuit, wherein the oxygen gas concentration in the recirculation chamber of the trocar is in direct correlation to carbon dioxide gas concentration within the patient's abdominal cavity, wherein the control unit maintains the carbon dioxide gas concentration in the abdominal cavity within a predetermined range based on the oxygen gas concentration in the recirculation chamber of the trocar, and increases an insufflation flow rate to the abdominal cavity through the trocar if the carbon dioxide gas concentration in the abdominal cavity falls below a predetermined level as a result of leakage, by controlling the operation of the compressor, and wherein the insufflation flow rate will not be lower than a smoke evacuation level, wherein the gas circuit that includes the recirculation chamber includes a pressure line and a suction line connected by the compressor for circulating gas, wherein the oxygen gas sensor is in the gas circuit downstream of where the suction line connects through a filter interface and filter cartridge to the recirculation chamber and/or wherein the oxygen gas sensor is in the gas circuit upstream of where the pressure line connects through the filter interface and filter cartridge to the recirculation chamber.

2. A surgical gas delivery device configured for insufflation and smoke evacuation through a gas sealed trocar having a recirculation chamber therein, the device comprising:
a device housing communicating with a patient's abdominal cavity through a gas circuit that includes a recirculation chamber of a gas sealed trocar and a compressor for circulating gas to and from the recirculation chamber of the trocar, the device housing supporting a gas composition unit having an oxygen gas sensor for monitoring oxygen gas concentration in the recirculation chamber of the trocar and a flow regulator communicating with the compressor for controlling an insufflation flow rate to the patient's abdominal cavity through the trocar based upon the oxygen gas concentration in the recirculation chamber of the trocar, wherein the insufflation flow rate will not be lower than a selected smoke evacuation level, wherein the gas circuit that includes the recirculation chamber includes a pressure line and a suction line connected by the compressor for circulating gas, wherein the oxygen gas sensor is in the gas circuit downstream of where the suction line connects through a filter interface and filter cartridge to the recirculation chamber and/or wherein the oxygen gas sensor is in the gas circuit upstream of where the pressure line connects through the filter interface and filter cartridge to the recirculation chamber.

3. A surgical gas delivery device configured for insufflation and smoke evacuation through a gas sealed trocar having a recirculation chamber therein, the device comprising:

a device housing communicating with a patient's abdominal cavity through a gas circuit that includes a recirculation chamber of a gas sealed trocar and a compressor for circulating gas to and from the recirculation chamber of the trocar, the device housing supporting a computer-controlled control unit having an oxygen gas sensor for monitoring oxygen gas concentration in the gas circuit, wherein the oxygen gas concentration in the recirculation chamber of the trocar is in direct correlation to carbon dioxide gas concentration within the patient's abdominal cavity, wherein the control unit maintains the carbon dioxide gas concentration in the abdominal cavity within a predetermined range based on the oxygen gas concentration in the recirculation chamber of the trocar, and increases an insufflation flow rate to the abdominal cavity through the trocar if the carbon dioxide gas concentration in the abdominal cavity falls below a predetermined level as a result of leakage, by controlling the operation of the compressor, and wherein the insufflation flow rate will not be lower than a smoke evacuation level, wherein the gas circuit that includes the recirculation chamber is a first gas circuit, and further comprising a second gas circuit operatively connected to the control unit for insufflating the abdominal cavity, wherein the control unit is operatively connected to the first and second gas circuits to control the insufflation flow rate in the second gas circuit based on oxygen gas concentration in the first gas circuit as monitored by the oxygen gas sensor.

4. A surgical gas delivery device configured for insufflation and smoke evacuation through a gas sealed trocar having a recirculation chamber therein, the device comprising:

a device housing communicating with a patient's abdominal cavity through a gas circuit that includes a recirculation chamber of a gas sealed trocar and a compressor for circulating gas to and from the recirculation chamber of the trocar, the device housing supporting a gas composition unit having an oxygen gas sensor for monitoring oxygen gas concentration in the recirculation chamber of the trocar and a flow regulator communicating with the compressor for controlling an insufflation flow rate to the patient's abdominal cavity through the trocar based upon the oxygen gas concentration in the recirculation chamber of the trocar, wherein the insufflation flow rate will not be lower than a selected smoke evacuation level, wherein the gas circuit that includes the recirculation chamber is a first gas circuit, and further comprising a second gas circuit operatively connected to a control unit for insufflating the abdominal cavity, wherein the control unit is operatively connected to the first and second gas circuits to control the insufflation flow rate in the second gas circuit based on oxygen gas concentration in the first gas circuit as monitored by the oxygen gas sensor.

\* \* \* \* \*